United States Patent [19]

Warren, III et al.

[11] Patent Number: 5,328,825
[45] Date of Patent: Jul. 12, 1994

[54] NUCLEIC ACID PROBE, TEST KIT AND DIAGNOSTIC AND PURIFICATION METHODS

[75] Inventors: Harold C. Warren, III, Rush; John B. Findlay, Rochester; Marlene M. King, Penfield, all of N.Y.

[73] Assignee: Eastman Kodak Company, Rochester, N.Y.

[21] Appl. No.: 847,447

[22] Filed: Mar. 6, 1992

Related U.S. Application Data

[63] Continuation of Ser. No. 471,168, Jan. 26, 1990, abandoned.

[51] Int. Cl.$^5$ .......................... C12Q 1/68; C07H 21/04
[52] U.S. Cl. ............................. 435/6; 435/5; 435/91.2; 536/24.3; 935/78
[58] Field of Search ................ 435/6, 5, 91.2; 536/27, 536/24.3, 25.4; 935/77, 78, 91

[56] References Cited

U.S. PATENT DOCUMENTS

| | | | |
|---|---|---|---|
| 4,591,571 | 5/1986 | Kuboyama et al. | 436/533 |
| 4,683,195 | 7/1987 | Mullis | 435/6 |
| 4,713,326 | 12/1987 | Dattagupta et al. | 435/6 |
| 4,775,619 | 10/1988 | Urdea | 435/6 |
| 4,812,414 | 3/1989 | Warren et al. | 436/533 |
| 4,828,978 | 5/1989 | Warren | 435/5 |

FOREIGN PATENT DOCUMENTS

| | | |
|---|---|---|
| 70687 | 1/1983 | European Pat. Off. |
| 8801302 | 2/1988 | World Int. Prop. O. |

Primary Examiner—Margaret Parr
Assistant Examiner—Carla Myers
Attorney, Agent, or Firm—J. Lanny Tucker

[57] ABSTRACT

An oligonucleotide is linked to a particle through a protein or carbohydrate to form a water-insoluble nucleic acid probe. The protein or carbohydrate has a pI of about 6 or less, and has been chemically modified with an acylating, alkylating or sulfonylating agent. The particle surface is substantially free of other proteins or carbohydrates. The probe is useful in various diagnostic and purification methods wherein hybridization of the oligonucleotide with a target nucleic acid is possible. In one instance, the probe can be used to capture a DNA strand which has been amplified using polymerase chain reaction techniques.

19 Claims, No Drawings

NUCLEIC ACID PROBE, TEST KIT AND DIAGNOSTIC AND PURIFICATION METHODS

This is a continuation of application Ser. No. 471,168, filed Jan. 26, 1990, now abandoned.

FIELD OF THE INVENTION

This invention relates to a water-insoluble reagent composed of a low pI protein or carbohydrate covalently attached to a particle, and to a nucleic acid probe prepared therefrom. It also relates to methods for isolating and capturing target nucleic acids, or to diagnostic methods. This invention is useful is genetic research and engineering, diagnostic assays, DNA sequencing and the synthesis of nucleic acids and structural genes.

BACKGROUND OF THE INVENTION

One important characteristic of nucleic acids, which form the genetic material of all living organisms, is their ability to form sequence-specific hydrogen bonds (that is, hybridize) with a nucleic acid having a complementary nucleotide sequence. This ability of nucleic acids to hybridize with complementary strands of nucleic acids has been used to advantage in what are known as hybridization assays, and in DNA purification techniques.

In a hybridization assay, a nucleic acid having a known sequence is used as a probe in a test sample to hybridize with a "target" nucleic acid having a complementary nucleic acid sequence. Labelling the probe allows for detection of the hybrid, and correspondingly, the target nucleic acid. Some hybridization assays are known as "sandwich" assays and involve the use of two probes, one labeled as noted above, and a second "capture" probe which is immobilized in some manner on a substrate (such as a filter, sheet or particle).

Because all strains of a particular organism or vital-infected cell share a genetic component in the form of nucleic acids, hybridization assays are valuable research and diagnostic tools for detection of and diagnosis of various disease states in humans, animals and plants. Additionally, the ability to probe for a specific nucleotide sequence is of potential value in the identification and diagnosis of human genetic disorders.

In the field of biochemistry and molecular biology, the purification or isolation of nucleic acids in a mixture thereof is often important for research and synthesis of genetic materials. A number of procedures have been developed whereby nucleic acids are isolated in affinity chromatography by using complementary strands attached to solid carriers.

The attachment of oligonucleotides to supports of various kinds has been accomplished in a number of ways, as noted for example in EP-B-0 070 687 (published Jan. 26, 1983) and references noted therein. Most of these techniques require the modification of the support or oligonucleotide or both in order to have suitable covalent bonding.

U.S. Pat. No. 4,713,326 (issued Dec. 15, 1987 to Dattagupta et al) describes binding nucleic acids to solid supports using a photochemically reactive intercalator compound such that upon irradiation, the nucleic acid is chemically linked to the support. Other linking groups, both photochemical or not, have also been used to connect oligonucleotides to solid supports, such as particles (see for example, WO-A-88/01302, published Feb. 25, 1988).

In some instances, nucleic acids can be directly attached to particles to prepare probes such as when the particles have surface carboxylic acid groups. However, this is not always easy nor convenient. Moreover, due to the hydrophobic nature of the particles having such reactive groups, and the nature of the oligonucleotides, molecules of the oligonucleotides adsorb to the particles after being covalently attached thereto. Such adsorption prevents efficient hybridization of the oligonucleotide with complementary nucleic acids.

It would be desirable to have an efficient means for hybridization or purification of nucleic acids using a water-insoluble probe.

SUMMARY OF THE INVENTION

The present invention provides a water-insoluble reagent comprising a water-insoluble particle having covalently attached thereto a non-immunoreactive protein or carbohydrate having a pI of about 6 or less, the protein or carbohydrate having been chemically modified with an acylating, alkylating or sulfonylating agent, the surface of the particle being substantially free of other proteins or carbohydrates.

The problems noted above concerning known probes are overcome with a water-insoluble nucleic acid probe comprising an oligonucleotide which is attached to a water-insoluble particle through a linking group which is a protein or carbohydrate having a pI of about 6 or less, the protein or carbohydrate having been chemically modified with an acylating, alkylating or sulfonylating agent to provide groups for covalent reaction with the oligonucleotide, and being covalently attached to the particle surface which is substantially free of other proteins or carbohydrates.

Moreover, a method for capturing and isolating a target nucleic acid comprises:

A. contacting a test sample suspected of containing a target nucleic acid with the water-insoluble nucleic acid probe described above, the oligonucleotide of the probe being substantially complementary to the target nucleic acid, the contacting being carried out under hybridization conditions so that hybridization of the target nucleic acid and the oligonucleotide is achieved to form a water-insoluble hybridization product, and B. isolating the hybridized product from the rest of the test sample.

Further, a method for the detection of a target nucleic acid comprises:

A. contacting a test sample suspected of containing a target nucleic acid with the water-insoluble nucleic acid probe described above, the oligonucleotide of the probe being substantially complementary to the target nucleic acid, the contacting being carried out under hybridization conditions so that hybridization of the target nucleic acid and the oligonucleotide is achieved to form a water-insoluble hybridization product, and B. detecting the hybridized product as an indication of the presence of the target nucleic acid in the test sample.

A diagnostic test kit comprises:

(a) the water-insoluble nucleic acid probe described above, and (b) one or more water-soluble primers or probes which are substantially complementary to a target nucleic acid, the target nucleic acid also being substantially complementary to the oligonucleotide of component (a).

The present invention provides useful water-insoluble nucleic acid probes formed from particles which can be used in a variety of research and diagnostic procedures, including nucleic acid purification, polymerase chain reaction amplification and hybridization assays. These probes are highly efficient because there is minimal adsorption of oligonucleotide to the particle surface. Yet, the oligonucleotide is effectively linked to the particles.

These advantages are achieved by linking the oligonucleotide to the particles through a protein or carbohydrate which has a pI less than or equal to about 6. This linking moiety is obtained by covalently attaching a protein or carbohydrate to the particle, followed by modification of the protein or carbohydrate to convert its pendant amino groups to carboxylic acid groups, thereby reducing its pI to about 6 or less. The oligonucleotide is then attached to the modified protein or carbohydrate.

DETAILED DESCRIPTION OF THE INVENTION

The present invention is directed to the use of certain probes for the purification, amplification or detection of one or more targeted nucleic acids in a test sample. Such samples can include cellular or vital material, hair, body fluids or other materials containing genetic DNA or RNA. While the primary purpose of purification might be to prepare materials for diagnostic procedures, purified nucleic acids can also be used to improve the efficiency of cloning DNA or messenger RNA, or for obtaining large amounts of the desired acid from a mixture of nucleic acids resulting from chemical synthesis. Other uses of purified target nucleic acids would be readily apparent to one skilled in the art.

Nucleic acids can be obtained from various sources including plasmids, naturally occurring DNA or RNA from any source (such as bacteria, yeast, viruses, plants and higher animals and humane). They may be extracted from various tissues including blood, tissue material or other sources known in the art using known procedures. The present invention is particularly useful for the detection of nucleic acid sequences found in viruses or cells of any organism, such as in genomic DNA, bacterial DNA, vital RNA, or DNA or RNA found in bacterial or vital infected cells. This invention is particularly useful for the detection of DNA from cells infected by HIV-I or other retroviruses.

In a preferred embodiment, the probe of this invention is used after a target nucleic acid has been amplified in a chain reaction which produces exponential quantities relative to the number of reaction steps involved, of at least one specific nucleic acid. The product will be a discrete nucleic acid duplex with termini corresponding to the ends of specific primers employed. Any source of nucleic acid can be utilized as the starting material provided it contains or is suspected of containing the specific nucleic acid targeted for detection. By "nucleic acid" is meant a fragment or an entire nucleic acid molecule. Moreover, more than one nucleic acid can be purified or detected simultaneously by using a specific set of water-insoluble probes, primers and labeled probes (described below) for each targeted nucleic acid.

As used herein in referring to primers, probes or nucleic acids to be detected, the term "oligonucleotide" refers to a molecule comprised of two or more deoxyribonucleotides or ribonucleotides, and preferably more than three. The exact size is not critical but depends upon many factors including the ultimate use or function of the oligonucleotide. The oligonucleotide may be derived synthetically or by cloning.

The term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleoside triphosphates) and an agent for polymerization such as a DNA polymerase, and suitable temperature and pH.

The term "probe" is used herein to refer to either capture or detection probes each of which comprise an oligonucleotide which is complementary to a target nucleic acid. A "capture probe" is a water-insoluble probe having an oligonucleotide connected to a water-insoluble substrate. The water-insoluble probe of this invention can be considered a "capture probe" A detection probe is usually water-soluble, although a capture probe can also be used for detection if desired. Generally, however, the water-soluble detection probes include an oligonucleotide which is detectably labeled in some manner (such as with a radioisotope, enzyme, fluorescent marker, chromogenic marker or other useful detection moiety).

In the practice of this invention, primers, probes and fragments are substantially complementary to a specific nucleic acid sequence of the targeted nucleic acid. By "substantially complementary" is meant that there are a sufficient number of bases on complementary materials that match so that hybridization will occur. It does not mean, however, that every base pair will match.

The probes of the present invention can be used in hybridization assays as they are known in the art. Generally, such assays involve the hybridization of a probe with a target nucleic acid, followed by detection of the hybrid product in some manner. In some embodiments, the probe is water-insoluble, and detectably labeled such as with a detectable marker associated with the probe (either as part of the oligonucleotide or as part of the water-insoluble particle). The hybrid is separated from unhybridized materials and detected in a suitable fashion. In other embodiments which are generally known as sandwich hybridization assays, two probes are used, one for capturing the target nucleic acid, and the other for detection. The hybrid "sandwich" is suitably detected. The various details of such assays are well known in the art including the references noted above in the Background of the Invention.

In all of the methods of using the probe of this invention, hybridization of the probe oligonucleotide and the target nucleic acid is critical. Hybridization generally occurs under conditions well known in the art, such as contact for at least about 1 minute, moderate agitation, a pH range of from about 5 to about 9 and a temperature of from about 0 to about 75° C. depending upon the $T_m$ of the probe. As is known in the art, $T_m$ refers to the temperature at which half of the probe molecules are hybridized and half are not.

In a preferred embodiment, the probe of this invention is used in the detection of a target nucleic acid using amplification techniques now widely known as polymerase chain reactions. The details of such techniques are provided in U.S. Pat. No. 4,683,195 (issued Jul. 28, 1987 to Mullis et al), U.S. Pat. No. 4,683,202 (issued Jul. 28, 1987 to Mullis) and EP-A-0 258 017 (published Mar. 2, 1988), all of which are incorporated herein by reference.

More particularly, for amplification and detection of a target nucleic acid, useful primers can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use. Naturally occurring primers isolated from biological sources are also useful (such as restriction endonuclease digests).

In some embodiments, at least one of the primers (or sets thereof) used in the detection method is labeled with a specific binding ligand. The term "labeled" refers to the fact that the ligand is attached to this primer in a manner such that it will not readily be detached. The specific binding ligand can be biotin or a derivative thereof, avidin or a derivative thereof, a leetin, a sugar, a protein, a hapten, a drug, or an immunological species, such as an antibody or an antigenic material.

The present invention is useful for amplification or detection of a targeted purified nucleic acid having two complementary strands. Most nucleic acid sequences of interest already are double-stranded, such as those found in DNA. However, single-stranded nucleic acid sequences, such as mRNA, can be similarly amplified and detected.

A specific nucleic acid sequence is produced using the nucleic acid containing that sequence as a template. If the acid contains two strands, it is necessary to separate the strands (called denaturation), either as a separate step or simultaneously with the formation of primer extension products. Denaturing can be accomplished using any suitable physical, chemical or enzymatic means as described in the art. Heating to a suitable temperature is a preferred means.

Once the separated strands are available for use, synthesis of additional nucleic acid strands can be carried out using two or more primers (at least one of which is labeled as described above) in a buffered aqueous solution at a pH of from about 7 to about 9. Preferably, a molar excess of the two primers is added to the buffered solution, and specific amounts are taught in the art. The deoxyribonucleotide triphosphates dATP, dCTP, dGTP and dTTP are also added to the synthesis mixture in adequate amounts and the resulting solution is heated to about 90°–100° C. for up to 10 minutes, and preferably from about 1 to about 4 minutes. Enzyme cofactors, such as magnesium or manganese ions, are also preferably present in molar excess to the triphosphates. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

The polymerization agent may be any compound, or combination of reagents, which will function to accomplish the synthesis of primer extension products, including enzymes (for example, E. coli DNA polymerase I, T4 DNA polymerase, Klenow polymerase, reverse transcriptase and others known in the art). Particularly useful enzymes are thermally stable enzymes, cloned or naturally occurring, such as those obtained from various Thermus bacterial species. Other polymerization agents are described in U.S. Pat. No. 4,683,202 (noted above).

Preferred thermal-stable enzymes are DNA polymerases from Thermus aquaticus such those as described in EP-A-0 258 017 (published Mar. 2, 1988). Other useful enzymes are described by Rossi et al, *Syst. Appl. Microbiol.*, 7(2-3), pp. 337–341, 1986. Many useful polymerases are commercially available. Generally, the synthesis of extension products will be initiated at the 3' end of each primer and proceed in the 5' to 3' direction along the template until synthesis is terminated. Some polymerization agents (for example, reverse transcriptase) may proceed in the 3' to 5' direction along the template.

The newly formed primer extension products comprising the newly synthesized strands and their respective primers form double-stranded molecules with the initial target strands which are used in the succeeding steps of the method. These strands are then separated by denaturation as described above to provide single-stranded molecules, onto which new nucleic acids are synthesized as described above. Additional reagents may be needed to keep the amplification procedure going, after which most of the extension products will consist of the specific nucleic acid sequence bounded by the two primers (that is, complementary products).

The steps of strand separation and extension product synthesis can be repeated as often as needed to produce the desired quantity of the specific nucleic acid needed for detection. Generally, the sequence of steps is repeated at least once, and preferably at least 10 to 50 times.

When it is desired to produce more than one targeted purified nucleic acid, the appropriate number of sets of primers are used in the general procedure described above.

At any point in the method of this invention after the generation of at least one primer extension product, that product can be hybridized with a detection probe (described below).

Generally, once a desired amount of the nucleic acid sequence of interest has been generated and the primer extension products are separated for a last time, the first primer extension product is contacted with a water-soluble detection probe which is labeled for detection and is complementary thereto to form a product. The probe is an oligonucleotide which is complementary with the targeted nucleic acid sequence. The oligonucleotide can be of any suitable length of nucleic acids, but preferably it is from about 15 to about 40 nucleic acids. It is labeled (commonly at the 5' end) with any suitable detectable material. Procedures for attaching labels and preparing probes are well known in the art, for example, as described by Agrawal et al, *Nucleic Acid Res.*, 14, pp. 6227–45 (1986). Useful labels include radioisotopes, electron-dense reagents, chromogens, fluorogens, phosphorescent moieties, ferritin and other magnetic particles, biotin, avidin, chemiluminescent moieties and enzymes (which are preferred). Useful enzymes include glucose oxidase, peroxidase, uricase, alkaline phosphatase and others known in the art. Substrates and dye forming compositions for such enzymes are well known.

In a particularly preferred embodiment, the label is peroxidase, and at some point in the assay, hydrogen peroxide and suitable dye-forming compositions are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide. A particularly useful dye-providing composition is illustrated in the examples below and in EP-A-0 308 236 (published Mar. 22, 1989).

Detection of the presence of the probe which is in the complementary product can be achieved using suitable and known detection equipment and procedures. Certain probes may be visible to the eye without the use of detection equipment. It is also useful for the method to be carried out in a suitable container. The most crude container would be a test tube, flask or beaker, but more sophisticated containers have been fashioned in order to facilitate automated procedures for performing the method.

In another embodiment, the amplified target nucleic acid is detected by using a primer which has a specific binding ligand, such as biotin or avidin, conjugated thereto. This ligand can be reacted with its receptor molecule (that is, the corresponding reactive material) which is suitably labeled as described above. For, example, a biotinylated primer can be detected using an enzyme-labeled streptavidin molecule. Other specific binding pairs, such as antibody-antigen, antibody-hapten, sugar-lectin, can be similarly used.

In order for the amplified target nucleic acid product to be detected, it is hybridized with a capture probe (as noted above). The resulting insolubilized complexed product can be separated from uncomplexed materials by filtration, centrifugation, washing or other suitable separation techniques.

Particularly useful separation means are microporous filter membranes such as the polyamide membranes marketed by Pall Corp. (for example as LoProdyne TM or Biodyne TM membranes). They can be used uncoated or precoated with surfactants or other materials which facilitate the analytical procedures.

The membranes can be used as a separate substrate with suitable containers for carrying out other steps of the assay. Preferably, however, they are mounted in test devices. Various test devices are known in the art including those described in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike) and U.S. Pat. No. 4,446,232 (issued May 1, 1984 to Liotta). Particularly useful devices are described in copending U.S. patent application Ser. No. 98,248 (filed Sep. 18, 1987 by Hinckley et al), now abandoned.

Thus, in a preferred embodiment for the detection of a target nucleic acid, the method comprises:

A. amplifying a target nucleic acid in a test specimen in the presence of complementary primers, deoxyribonucleotide triphosphates and a polymerization agent, B. contacting the amplified target nucleic acid with a water-insoluble nucleic acid probe comprising an oligonucleotide which is attached to a water-insoluble particle through a linking group which is a protein or carbohydrate having a pI of about 6 or less, the protein or carbohydrate having been chemically modified with an acylating, alkylating or sulfonylating agent to provide groups for covalent reaction with the oligonucleotide, and being covalently attached to the particle surface which is substantially free of other proteins or carbohydrates, to form an immobilized hybridized product of target nucleic acid and the water-insoluble probe, C. separating the immobilized product from nonimmobilized materials, and D. detecting the immobilized product as an indication of the amount of target nucleic acid in the specimen.

The water-insoluble reagent of this invention, which can be used to prepare the probe of this invention, comprises a protein or carbohydrate having a pI of about 6 or less covalently attached to water-insoluble particles. Useful particles can be prepared from any suitable synthetic or naturally-occurring material which does not dissolve or swell appreciably in water. Suitable particulate materials include, but are not limited to, cellulosic materials, glass, ceramics, metals and various polymers. They can be of any useful shape and size including spherical, ellipsoidal, cubic, irregular or flat and have an average large dimension (for example, diameter) of from about 0.1 to about 10 $\mu$m although larger or smaller sizes may be useful in certain instances.

Preferably, the particles are spherical and have an average diameter of from about 0.1 to about 10 $\mu$m, and are composed of synthetic polymers which have groups on the surface which will react with proteins or carbohydrates. Useful reactive groups include, but are not limited to, carboxy, amino, sulfhydryl, aldehyde, activated 2-substituted ethylsulfonyl, vinylsulfonyl, active halogen atoms, vinylsulfonylalkylene, nitroaryl, esters and others readily apparent to one skilled in the art. Particularly useful reactive groups include carboxy, active halogen atoms, vinylsulfonyl, vinylsulfonylalkylene and activated 2-substituted ethylsulfonyl. Monomers having activated 2-substituted ethylsulfonyl groups are most preferred. Some of these materials are described in detail in EP-A-0 302 715, incorporated herein by reference. Such monomers are either commercially available or readily synthesized by a skilled chemist.

The low pI proteins or carbohydrates are covalently attached to the particles noted above. Generally, only one protein or carbohydrate is used, although mixtures are feasible if desired. These materials have a pI of about 6 or less and are water-soluble. The term pI (or isoelectric point) is known as the pH at which there is an equal number of positive and negative charges in a molecule so that the molecule is neutral in charge. The pI of a protein or carbohydrate can be measured using standard materials and procedures. For example, it can be measured by isoelectric focusing using an LKB Ampholine PAG plate (available from LKB-Produkter AB, Bromma, Sweden), pH range 3.5-9.5, and standard calibrators.

The proteins and carbohydrates useful herein can be immunoreactive materials, that is antibodies or antigenic materials which produce an immunoresponse in a suitable host mammal, and which will participate in antibody-antigen reactions. Preferably, however, the proteins and carbohydrates are non-immunoreactive, meaning that they will not participate to an appreciable extent in immunological reactions.

Useful water-soluble non-immunoreactive proteins include casein derivatives or other protein derivatives which are negatively charged, for example succinylated casein, glutarylated casein, succinylated bovine serum albumin, succinylated collagen and others apparent to one skilled in the art. Such derivatives are generally obtained from acylation, alkylation or sulfonation of casein, bovine serum albumin, collagen and other proteins having suitable amine groups to provide reactive carboxy groups on the protein or carbohydrate. Such protein and carbohydrate to be modified are generally readily available commercially.

Acylating agents and conditions are described, for example, in U.S. Pat. No. 4,591,571 (issued May 27, 1986 to Kuboyama et al), and include anhydrides, acyl halides and esters derived from dicarboxylic and polycarboxylic acids. Succinic anhydride is a preferred acylating agent. The succinylation of casein is described in Example 1 below.

Useful alkylating and sulfonating agents include, but are not limited to, bromoacetic acid, chloroacetic acid, fluoronitrobenzene, m-(chlorosulfonyl)benzoic acid, bromomalonic acid, bromopropionic acid and p-(chlorosulfonyl)benzoic acid.

The conditions for acylating, alkylating or sulfonylating a protein generally include the use of a borate buffer (0.05 molar, pH 8.5) at room temperature using about three times the amount of modifying agent to the amount (by weight) of protein.

The protein is modified for use in this invention after its covalent attachment to the particles noted above.

Useful water-soluble carbohydrates having a low pI include, but are not limited to, carboxymethyl cellulose, carboxyethyl cellulose and others readily apparent to one skilled in the art. Such materials are generally commercially available.

A group of preferred low pI proteins and carbohydrates includes succinylated casein, succinylated collagen, glutarylated casein, succinylated bovine serum albumin, carboxymethyl cellulose and carboxyethyl cellulose. Succinylated casein is particularly preferred.

The water-insoluble reagent of this invention is generally prepared by first reacting the protein or carbohydrate with the surface reactive groups on the particles to attach them. The proteins can be reacted directly with the surface groups, or reacted with linking moieties which are on the particles. Conditions for attaching the proteins or carbohydrates is generally carried out by contacting the particles and protein (or carbohydrate) for a period of time (generally at least six hours) under pH and temperature conditions which facilitate reaction. Useful pH is generally from about 5 to about 9, and the temperature is generally from about 20° to about 40° C. A representative procedure is described in Example 1 below.

Once the protein or carbohydrate has been modified to provide reactive carboxy groups, an oligonucleotide is attached thereto. The oligonucleotides used to make probes are described generally above. They are generally from 15 to 50 nucleotides in length, and are complementary to a nucleic acid sequence of the target nucleic acid. They are attached to the modified protein or carbohydrate generally by carbodiimide activation of the carbonyl group in 2-(N-morpholino)ethanesulfonic acid buffer (pH 6). A representative procedure for preparing a probe is shown in Example 2 below.

As noted above, this probe can also have a detectable label associated therewith, meaning that a detectable label can be a part of the probe in some fashion. For example, the protein or carbohydrate linkage or oligonucleotide can be labeled, such as with an enzyme or radioisotope using known chemistry. Alternatively, a marker can be within the particle or on its surface, such as in an embodiment having a particle containing imbibed dye.

The particles of the probe do not have any proteins or carbohydrates attached thereto in any manner other than the low pI materials described herein. By "substantially free" is meant that less than about five percent of the particle surface area is covered by other proteins or carbohydrates.

The probe of this invention can be supplied as a component of a diagnostic test kit, along with suitable reagents, test equipment and instructions needed for a given diagnostic test. Useful reagents which can be included in the test kit include, but are not limited to, water-soluble probes or primers which are also complementary to the target nucleic acid, wash solutions, dye-providing compositions, enzyme substrates and polymerase chain reaction reagents.

The following examples are provided to illustrate the practice of the present invention. There is no intention to limit the invention thereby. All percentages are by weight, unless otherwise indicated.

EXAMPLE 1: PREPARATION OF WATER-INSOLUBLE REAGENT

A reagent useful in the practice of this invention was prepared by the following procedure.

Polymeric particles comprising poly[styrene-co-m & p-(2-chloroethylsulfonylmethyl)styrene](95.5:4.5 molar ratio, 2.2 μm average size) were prepared by the methods described in U.S. patent application Ser. No. 081,206 (filed Aug. 3, 1987 by Sutton et al), incorporated herein by reference.

Casein was attached to these particles in the following manner: A solution of casein (Sigma Chemical, 4.94 ml of 2.57 mg/ml in 0.05 molar borate buffer, pH 8.5), thimerosal (0.01%) and the noted suspension of polymeric particles (17.7 ml in borate buffer, 0.0637 g/ml) was rotated end-over-end for 16 hours at room temperature. The mixture was then centrifuged and the buffer solution was discarded. The resulting pellet was resuspended in glycine buffer (0.1 molar, 50 ml, pH 8.5) and thimerosal (0.01%). This mixture was centrifuged, and the resulting pellet was resuspended in glycine buffer (250 ml) to 0.45% solids.

A sample of the particle suspension (50 ml) containing 2.54 g of particles was washed three times with borate buffer (10 ml, 0.05 molar, pH 8.5), mixed with succinic anhydride (Sigma Chemical, 0.762 ml) in a solution of dimethyl sulfoxide (10 mg/ml) and allowed to react for four hours at room temperature to modify the casein molecules to provide carboxy groups. The mixture was centrifuged and the solution discarded. The resulting pellet was washed three time with glycine buffer (50 ml, 0.01 molar, pH 8.5), and resuspended in glycine buffer to 0.45% solids to provide the desired reagent.

EXAMPLE 2: PREPARATION OF A WATER-INSOLUBLE NUCLEIC ACID PROBE

A suspension of the reagent of Example 1 (15 ml, 0.0045 g/ml) in glycine buffer was centrifuged, and the pellet resuspended in 2-(N-morpholino)ethanesulfonic acid buffer (0.1 molar, pH 6). This procedure was repeated twice and the resulting pellet was mixed with 1-(3-dimethylaminopropyl)-3-ethylcarbodiimide hydrochloride (0.338 ml of a solution of 100 mg/ml in the same buffer) and the oligonucleotide having the sequence noted below (0.654 μl of a solution of 5.73

OD/ml of buffer). This suspension was rotated end-over-end for sixteen hours at room temperature and centrifuged, and the pellet was resuspended in nanopure water (15 ml). This centrifuging procedure was repeated three times, and the resulting pellet was suspended in water to provide a 0.45% solid suspension of water-insoluble probe.

The probe oligonucleotide had the nucleic acid sequence (using standard base identification):

5'-ATCCTGGGATTAAATAAAATAG-TAAGAATGT-3'

EXAMPLE 3: DIAGNOSTIC ASSAY USING PROBE

The probe prepared in Example 2 was used to detect a target nucleic acid in the manner described below. This example demonstrates the detection of HIV-I DNA using what is termed a "flow through" procedure whereby a water-insoluble probe is immobilized on a filter membrane in a disposable test device. Hybridization with the HIV-I DNA target occurs to form a water-insoluble product, then water-soluble materials are washed through the filter membrane. The water-insoluble product is detected on the membrane surface.

Materials

A leuco dye solution was prepared containing 2-(4-hydroxy-3,5-dimethoxyphenyl)-4,5-bis(4-methoxyphenyl)imidazole as follows: Solid leuco dye (to make a 0.1% solution) was dissolved in a solution of 20% poly(vinylpyrrolidone) in sodium phosphate buffer (5 mmolar). This solution was then added to a solution containing hydrogen peroxide (10 mmolar), 4'-hydroxyacetanilide electron transfer agent (5 mmolar) and diethylenetriaminepentaacetic acid chelating agent (10 μmolar) in sodium phosphate buffer to produce a final concentration of 1% poly(vinylpyrrolidone) and 0.005% leuco dye.

Succinylated casein was prepared by reacting casein with an equal weight of succinic anhydride for four hours at 25° C. then purifying the product by dialysis.

The target DNA fragment detected in the example was a 180 nucleotide segment of the gag region (core protein) of the HIV-I genome cloned into a derivative of M13 vector and prepared using standard procedures.

The primers used in the amplification of the predetermined DNA strands had the following nucleotide sequences using the standard abbreviations for adenine (A), guanine (G), thymine (T) and cytosine (C):

5'-X-TTTGGTCCTTGTCTTATGT-CCAGAATGC-3' and

5'-ATAATCCACCTATCCCAGTAG-GAGAAAT-3' wherein X represents biotintetraethylene glycol spacer, prepared and attached by procedures described in WO-A-89/02931, incorporated by reference.

DNA polymerass was isolated from Thermus aquaticus according to the procedures described in EP-A-0 258 017 (1 unit corresponds to 10 Moles of dNTP incorporated into the primer extension product in 30 minutes at 37° C.).

A streptavidin-horseradish peroxidase conjugate was obtained from Zymed Labs (San Francisco), and was diluted 1:8000 with a phosphate buffered saline solution containing casein (0.5%), 3-(N-morpholino)-propanesulfonic acid buffer (100 mmolar, pH 7.5) and preservative (0.01%). The final conjugate concentration was 156 ng/ml. The phosphate buffered saline solution contained sodium phosphate (25 mmolar, pH 7.3) and sodium chloride (75 mmolar).

The water-insoluble probe of Example 2 (1 pl of 0.45% suspension) was deposited in a defined region (less than about 2 mm²) of each of several microporous membranes (Biodyne ™ A nylon membranes coated with 1 g/m² succinylated casein) located in test wells of Surecell ™ disposable test devices (Eastman Kodak Co.). The probe suspension was allowed to dry for about 30 minutes at room temperature. The resulting test articles were then used in the assay described below.

Assay Procedure

To a buffer solution containing tris(hydroxymethyl)aminomethane buffer (10 mmolar, pH 8), potassium chloride (50 mmolar), magnesium chloride (10 mmolar) and gelatin (10 μg) were added the primers described above (100 pmoles of each), dNTPs (1.5 mmolar of each), the polymerase described above (7.5 units) and human placenta DNA (Sigma, 1 pg). In addition, the DNA target ($10^{-16}$ molar) described above was added, and the total volume was 100 μl.

A control (100 μl) was prepared containing human placenta DNA (10 μg/ml) containing the B-globin gene as target, and the appropriate primers, specific for B-globin DNA which are known in the art, one primer being biotinylated.

Each solution described above was placed into a polypropylene microcentrifuge tube, primer extension products were formed, and amplification promoted using 30 consecutive thermal cycles as follows:

| 70° C. rising to 95° C. | 1 minute |
|---|---|
| 95° C. | 0.5 minute (denature) |
| 95° C. lowering to 55° C. | 1.25 minutes |
| 55° C. | 0.5 minute (hybridize) |
| 55° C. rising to 70° C. | 0.75 minute |
| 70° C. | 1 minute (extend) |

After amplification through the 30 thermal cycles, 5 μl aliquots of each mixture were added to a solution (95 μl) containing tris(hydroxymethyl)aminomethane buffer (10 mmolar, pH 8), potassium chloride (50 mmolar), magnesium chloride (10 mmolar) and gelatin (1 μg/10 ml solution), heat denatured (5 minutes at 95° C.), then added to the test wells of the Surecell ™ test devices described above (about 95 μl of each solution in each well).

Tape was placed over each well to seal them, and the devices were incubated at 42° C. for 5 minutes to hybridize the amplified HIV-I DNA fragment to the water-insoluble probe immobilized in the test wells. The tape was then removed off each test well, followed by washing with a buffered solution (250 μl) containing phosphate buffer (10 mmolar, pH 7.4), sodium chloride (150 mmolar), ethylenediaminetetraacetic acid (1 mmolar) and sodium decyl sulfate (1%) at 55° C.

The peroxidase conjugate described above (50 μl, 7.8 ng) was added to each test well, and the devices were incubated at room temperature for 2 minutes. A second wash (250 μl) was carried out using the buffered solution noted above. The leuco dye solution (100 μl) was added to each test well followed by another incubation at room temperature for 2 minutes. The resulting dye-forming reaction was stopped by the addition of sodium azide (100 μl of 0.1%), and the resulting dye was observed on the membranes.

The amount of dye formed on the membrane in the assay was visually graded on a scale of from 0 to 5 (zero being no density and 5 being the highest density). The background value was obtained from a density reading on the membrane area where no water-insoluble probe was present. The dye density reading for the assay was determined to be about 4.8 while the background density was about 0.5.

The invention has been described in detail with particular reference to preferred embodiments thereof, but it will be understood that variations and modifications can be effected within the spirit and scope of the invention.

We claim:

1. A water-insoluble nucleic acid probe comprising an oligonucleotide which is attached to a water-insoluble particle through a linking group which is a chemically modified protein or a chemically modified carbohydrate having a pI of about 6 or less, said chemically modified protein having been derived from a protein having pendant amino groups which have been chemically modified with an acrylating, alkylating or sulfonylating agent to provide carboxylic acid groups for covalent reaction with said oligonucleotide, and said chemically modified carbohydrate having been modified to have pendant carboxylic acid groups, and said chemically modified protein or chemically modified carbohydrate being covalently attached to said particle surface which is substantially free of other proteins or carbohydrates.

2. The probe of claim 1 wherein said chemically modified protein or carbohydrate is succinylated casein, glutarylated casein, succinylated collagen, succinylated bovine serum albumin, carboxymethyl cellulose or carboxyethyl cellulose.

3. The probe of claim 1 wherein said particle is a synthetic polymeric particle having an average diameter of from about 0.1 to about 10 μmeter, which polymeric particles are prepared from monomers having reactive groups selected from the group consisting of carboxy, active halogen atoms, activated 2-substituted ethylsulfonyl, vinylsulfonyl and vinylsulfonylalkylene groups.

4. The probe of claim 1 wherein said oligonucleotide is a nucleic acid sequence which is complementary with a strand of HIV-I DNA.

5. The probe of claim 1 having a detectable label associated therewith.

6. The probe of claim 1 wherein said particle is a synthetic polymer particle having an average diameter of from about 0.1 to about 10 μm and being prepared from a monomer having activated 2-substituted ethylsulfonyl groups, the oligonucleotide is complementary to a strand of HIV-I DNA, and said oligonucleotide is attached to said particle through succinylated casein which is covalently attached to said particle surface which is substantially free of other proteins or carbohydrates.

7. A method for capturing and isolating a target nucleic acid comprising:

A. contacting a test sample suspected of containing a target nucleic acid with a water-insoluble nucleic acid probe comprising an oligonucleotide which is attached to a water-insoluble particle through a linking group which is a chemically modified protein or a chemically modified carbohydrate having a pI of about 6 or less, said chemically modified protein having been derived from a protein having a pendant amino groups which have been chemically modified with an acylating, alkylating or sulfonylating agent to provide carboxylic acid groups for covalent reaction with said oligonucleotide, and said chemically modified carbohydrate having been modified to have pendant carboxylic acid groups, and said chemically modified protein or chemically modified carbohydrate being covalently attached to said particle surface which is substantially free of other of other proteins or carbohydrates, said oligonucleotide being complementary to said target nucleic acid, said contacting being carried out under hybridization conditions so that hybridization of said target nucleic acid and said oligonucleotide is achieved to form a water-insoluble hybridization product, and B. isolating said hybridized product from the rest of said test sample.

8. A method for the detection of a target nucleic acid comprising:

A. contacting a test sample suspected of containing a target nucleic acid with a water-insoluble nucleic acid probe comprising an oligonucleotide which is attached to a water-insoluble particle through a linking group which is a chemically modified protein or a chemically modified carbohydrate having a pI of about 6 or less, said chemically modified protein having been derived from a protein having pendant amino groups which have been chemically modified with an acylating, alkylating or sulfonylating agent to provide carboxylic acid groups for covalent reaction with said oligonucleotide, and said chemically modified carbohydrate having been modified to have pendant carboxylic acid groups, and said chemically modified protein or chemically modified carbohydrate being covalently attached to said particle surface which is substantially free of other proteins or carbohydrates, said oligonucleotide being complementary and specific to said target nucleic acid, said contacting being carried out under hybridization conditions so that hybridization of said target nucleic acid and said oligonucleotide is achieved to form a water-insoluble hybridization product, and B. detecting said hybridized product as an indication of the presence of said target nucleic acid in said test sample.

9. The method of claim 8 wherein said water-insoluble nucleic acid probe has a detectable label associated therewith for detection of said hybridized product.

10. The method of claim 8 carried out as a sandwich hybridization assay wherein said water-insoluble nucleic probe is an unlabeled capture probe, and said target nucleic acid is also hybridized with a water-soluble, labeled probe.

11. The method of claim 10 wherein said water-soluble probe is labeled with an enzyme.

12. The method of claim 10 wherein said water-soluble probe is labeled with biotin, and said probe is reacted with a conjugate composed of avidin and an enzyme.

13. The method of claim 8 wherein said target nucleic acid is amplified using polymerase chain reaction prior to contact in step A.

14. The method of claim 8 wherein said water-insoluble particle is a synthetic polymeric particle having an average diameter of from about to about 10 μmeter, and are prepared from monomers having reactive groups selected from the group consisting of carboxy, active halogen, activated 2-substituted ethylsulfonyl, vinylsulfonyl and vinylsulfonylalkylene groups.

15. The method of claim 8 wherein said chemically modified protein or carbohydrate is succinylated casein, glutarylated casein, succinylated collagen, succinylated bovine serum albumin, carboxymethyl cellulose or carboxyethyl cellulose.

16. The method of claim 8 for the detection of a HIV-I DNA wherein said oligonucleotide is complementary to HIV-I DNA.

17. A method for the detection of a target nucleic acid, said method comprising:
  A. amplifying a target nucleic acid in a test specimen in the presence of complementary primers, deoxyribonucleotide triphosphates and a polymerization agent,
  B. contacting said amplified target nucleic acid with a water-insoluble nucleic acid probe comprising an oligonucleotide which is attached to a water-insoluble particle through a linking group which is a chemically modified protein or a chemically modified carbohydrate having a pI of about 6 or less,
  said chemically modified protein having been derived form a protein having pendant amino groups which have been chemically modified with an acrylating, alkylating or sulfonylating agent to provide carboxylic acid groups for covalent reaction with said oligonucleotide, and said chemically modified carbohydrate having been modified to have pendant carboxylic acid groups, and said chemically modified protein or chemically modified carbohydrate being covalently attached to said particle surface which is free of other proteins or carbohydrates,
  to form an immobilized hybridized product of target nucleic acid and said water-insoluble probe,
  C. separating said immobilized product from nonimmobilized materials, and
  D. detecting said immobilized product as an indication of the amount of target nucleic acid in said specimen.

18. A diagnostic test kit comprising:
  (a) a water-insoluble nucleic acid probe comprising an oligonucleotide which is attached to a water-insoluble particle through a linking group which is a chemically modified protein or a chemically modified carbohydrate having a pI of about 6 or less,
  said chemically modified protein having been derived from a protein having pendant amino groups which have been chemically modified with an acrylating, alkylating or sulfonylating agent to provide carboxylic acid groups for covalent reaction with said oligonucleotide, and said chemically modified carbohydrate having been modified to have pendant carboxylic acid groups, and said chemically modified protein or chemically modified carbohydrate being covalently attached to said particle surface which is substantially free of other proteins or carbohydrates, and
  (b) a water-soluble primer or probe which is complementary and specific to a target nucleic acid, said target nucleic acid also being complementary and specific to said oligonucleotide of component (a).

19. The test kit of claim 18 further comprising reagents necessary for polymerase chain reaction on a target nucleic acid.

* * * * *

UNITED STATES PATENT AND TRADEMARK OFFICE
CERTIFICATE OF CORRECTION

PATENT NO. : 5,328,825
DATED : July 12, 1994
INVENTOR(S) : Harold C. Warren III, et al It is certified that error appears in the above-indentified patent and that said Letters Patent is hereby corrected as shown below:

Column 15, line 8 reads "average diameter of from about to about 10 µmeter, and"

should read --average diameter of from about 0.1 to about 10 µmeter, and--

Signed and Sealed this

Twenty-seventh Day of September, 1994

*Attest:*

BRUCE LEHMAN

*Attesting Officer*   *Commissioner of Patents and Trademarks*